May 2, 1933. L. REYMOND Plant Pat. 63
ROSE
Filed Oct. 27, 1932
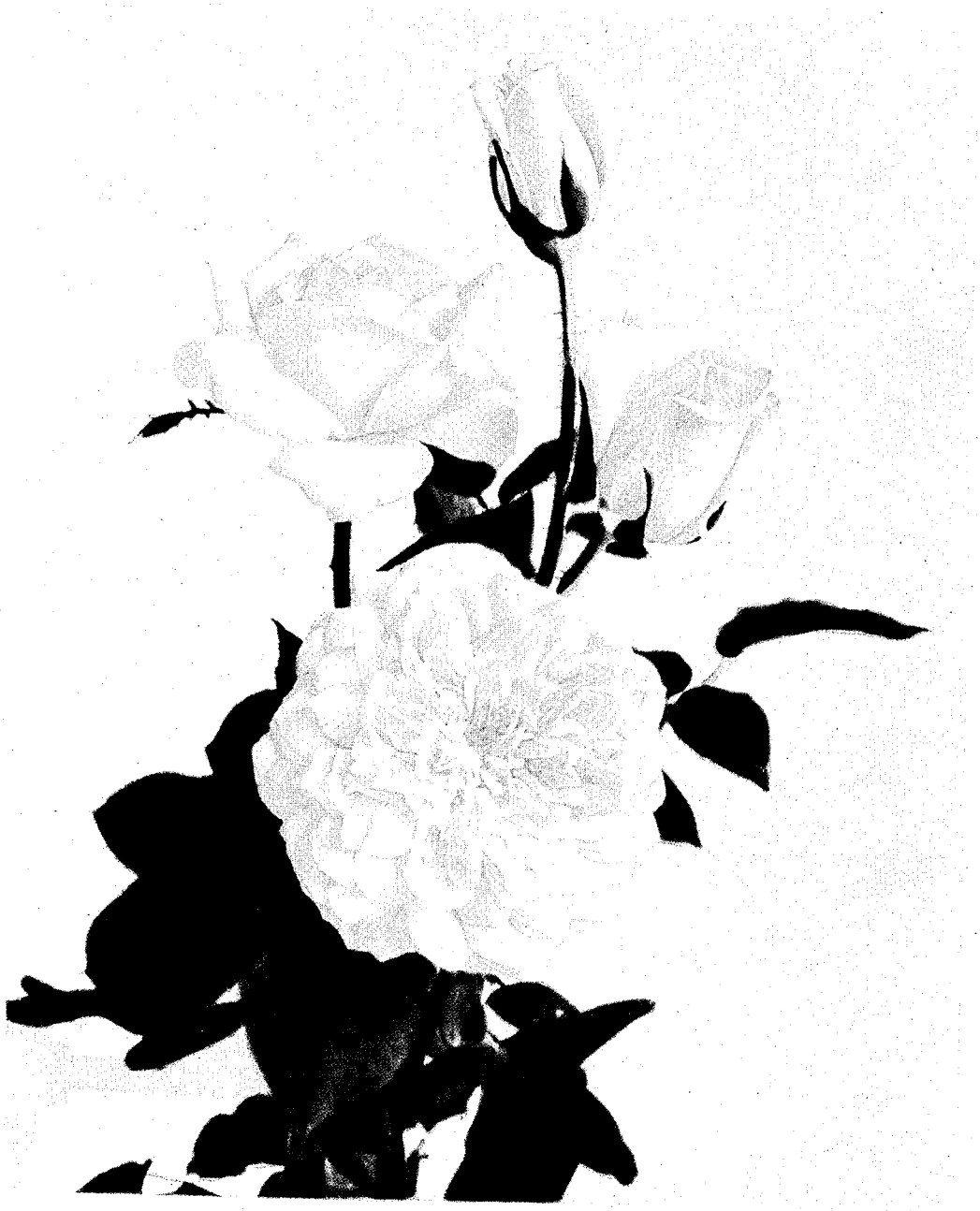
INVENTOR
L. Reymond
By Robb & Robb
ATTORNEYS Patented May 2, 1933

Plant Pat. 63

UNITED STATES PATENT OFFICE

LOUIS REYMOND, OF VILLEURBANNE, FRANCE, ASSIGNOR TO JACKSON & PERKINS COMPANY, OF NEWARK, NEW YORK

ROSE

Application filed October 27, 1932. Serial No. 639,903.

The present invention relates to a new variety and strain of rose, the novel characteristics of which reside particularly in the extremely large size of the bloom, the color unusual for the strain, the robustness of the plant and its tout ensemble.

The present rose originated from Souvenir de Claudius Pernet hybridized with the pollen of a seedling of Louise Catherine Breslau itself pollenized with the Hybrid Perpetual Paul Neyron. The various seedlings of this cross were recombined for several generations with the object of creating a rose of the Pernetiana yellow color of the size of Paul Neyron which is the largest rose known so far, with its intense centifolia perfume and at the same time retaining the main characters of the Pernetiana group; its continuity of bloom and usefulness as a bedding variety and for cut flowers. I had also in mind the important factor of eliminating the usual tendency of the Pernetianas to foliage diseases and inbreeding the hardiness and disease resistance of the ancestor Paul Neyron. This involved a long and tedious process of selection, hybridization and vegetative propagation, with the resultant variety herein disclosed.

The rose forming the subject matter of this application is considered novel in every particular, as to size, fragrance, hardiness, the characteristic of the health of foliage of the Paul Neyron variety, the form of the open flower similar to the Louise Catherine Breslau variety and the color resembling the Souvenir de Claudius Pernet in the center, while the bud and outer rim of the open flower is creamy with a faint blush.

It is a marked characteristic of this variety that the full open flower is extremely large, most often five inches, sometimes reaching six inches, in diameter in the greenhouse. This is in reality one of the largest roses in existence and fully as large as Paul Neyron at its best. It is full to the center, gracefully imbricated and the inner petals are small and lanceolate.

The rose is suitable for garden growing as well as in the greenhouse for florist purposes.

As a convenient summary the following detailed description of this new variety is given:

Parentage:—

Seedling.

*Seed parent.*—Souvenir de Claudius Pernet.

*Pollen parent.*—Seedling of Louise Catherine Breslau x Paul Neyron.

Classification:—

Botanic (name strains) Pernetiana hybrid under which it will be in commerce—Pernetiana hybrid.

*Flower*

Blooming habit:—

*Recurrent.*—Continuous.

Bud:—

*Size.*—Very large.

*Form.*—Very long, pointed. Not affected by wet or hot weather.

*Color.*—When petals first divide, creamy with a blush; when petals begin to unfurl, creamy with a blush; when half blown; inside of petals, yellow reverse of petals, creamy with a blush.

*Sepals.*—Branched, stand up.

*Calyx.*—Shape, pear. Size, large, broad. Aspect, smooth. No odor when rubbed.

*Peduncle.*—Length, very long. Aspect, rough. Color, light green. Strength, stiff, erect, heavy.

*Opening.*—Opens well, not affected by adverse conditions.

Bloom:—

*Size.*—Very large, average size when fully expanded 5″, often over 6″ in green houses.

*Borne.*—Singly.

*Stems.*—Long, strong.

*Form.*—When first open, high center. Permanence, flattens.

*Petalage.*—Very double. 150 petals under normal conditions.

*Color.*—Center of flower, deep yellow. Outer petals, creamy yellow with faint blush. Base of petals (aiglet) yellow. Inside of petals, yellow. Reverse of petals, center ones yellow, outer ones cream with blush. General tonality from a distance, yellow.

*Variegations.*—None.

*Discoloration.*—General tonality at end of first, second and third day, same.

Petals:—

*Texture.*—Thick, not affected by wet or hot weather.

*Appearance.*—Inside, satiny. Outside, satiny.

*Form.*—Outer ones round, inner ones lanceolate.

*Arrangement.*—Imbricated (regularly arranged shingle-like). Petaloids in center; many.

*Persistence.*—Drop off cleanly.

*Fragrance.*—Strong. Nature—"Old Rose perfume" (centifolia).

*Lastingness.*—On the plant, very long. As cut flower, very long.

Genital organs:—

*Stamens, anthers.*—Few. Color: yellow. Arrangement: mixed with petaloids.

*Stamens, filaments (threads).*—Short. Color: yellow.

*Pollen.*—Lemon yellow.

*Styles.*—Bunched, even length. Short, heavy.

*Stigmas.*—Color, white.

*Ovaries.*—Some protruding from calyx.

Fruit:—

Variety is generally sterile.

*Form.*—Round, depressed top, seeds protruding, bears very few fruits.

*Aspect.*—Smooth.

*Color at maturity.*—Orange.

*Sepals.*—Permanent; recurved.

*Plant*

Form:—

Bush.

Growth:—

Vigorous, branching.

Foliage:—

*Leaflets.*—Generally 5, sometimes 7.

*Size.*—Very large.

*Quantity.*—Normal.

*Color.*—New foliage: upper side, light green, under side, dull green. Old foliage: upper side, dark green, under side, dull green.

*Shape.*—Oval pointed, (lanceolate terminals).

*Texture.*—Upper side, glossy, flat. Under side, rough. Ribs and veins: ordinary.

*Edge.*—Serrated (saw toothed).

*Serration.*—Single.

*Leaf stem.*—Color, green. Under side, prickles.

*Stipules.*—Medium. Smooth.

*Disease resistance.*—Resistant.

Wood:—

*New wood.*—Color, light green. Bark: smooth.

*Old wood.*—Color, green. Bark: smooth.

Thorns:—(N. B. Thorns are divided into thorns, prickles and short needles.)

Thorns:

*Quantity.*—On main stalks from base, ordinary. On laterals from stalk, few.

*Form.*—Broad base. Medium. Hooked downward.

*Color when young.*—Green and red.

*Position.*—Irregular.

Prickles:

*Quantity.*—On main stalks, few. On laterals, few.

*Color.*—Green.

Short Needles:

*Quantity.*—On main stalks, none. On laterals, none.

I claim:

The new variety of rose characterized by the extremely large size of its bloom, the distinct yellow color thereof and the robustness of the plant, as shown and described.

In testimony whereof I affix my signature.

L. REYMOND.